| United States Patent [19] | [11] | 4,048,220 |
|---|---|---|
| Cardenas | [45] | Sept. 13, 1977 |

[54] PROCESS FOR PREPARATION OF 1,4-HALOALLYLIC ESTERS FROM DIENES

[75] Inventor: Carlos G. Cardenas, Jacksonville, Fla.

[73] Assignee: SCM Corporation, New York, N.Y.

[21] Appl. No.: 582,112

[22] Filed: May 30, 1975

[51] Int. Cl.$^2$ ............ C07C 67/04; C07C 67/24; C07C 67/28

[52] U.S. Cl. ............ 560/237; 260/405.6; 260/408; 560/241; 560/111

[58] Field of Search ............ 260/491, 497 R, 476 R, 260/405.6, 408

[56] References Cited

U.S. PATENT DOCUMENTS 2,511,870   6/1950   Oroshnik .................. 260/497 R
3,720,704   3/1973   Sakomura et al. .......... 260/491

*Primary Examiner*—Vivian Garner
*Attorney, Agent, or Firm*—Richard H. Thomas

[57] ABSTRACT

A process for the synthesis of 1,4-haloallylic esters from conjugated dienes which comprises preparing a reaction mixture of the conjugated diene, a halogenating agent, and a carboxylic acid and then adding to said reaction mixture a catalytic amount of a strong acid having a high dissociation constant. The invention is particularly described with reference to the synthesis of isoprene-1,4-chloroacetate(1-chloro-4-acetoxy-2-methyl-2-butene) from isoprene wherein a reaction mixture is prepared of isoprene with t-butyl hypochlorite in excess glacial acetic acid, to which is added $H_2SO_4$ followed by stirring at 50° C.

9 Claims, No Drawings

PROCESS FOR PREPARATION OF 1,4-HALOALLYLIC ESTERS FROM DIENES

The present invention relates to the preparation of unsaturated haloesters, e.g., a chloroallylic ester, and preferably to an improved method for the preparation of such esters from dienes.

The present invention will be described with reference to isoprene and to the preparation therefrom of isoprene-1,4-chloroacetate (1-chloro-4-acetoxy-2-methyl-2-butene) which has the structure

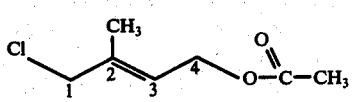

This compound may also be named 4-chloro-3-methyl-2-butene-1-yl acetate. It will be apparent to those skilled in the art that the invention also has applicability in the haloesterification of other olefinic materials such as butadiene and 1,3-pentadiene.

BACKGROUND OF THE INVENTION

Prior application Ser. No. 246,930, filed Apr. 24, 1972, now abandoned, by William Oroshnik, assigned to assignee of the present application, describes a new process for making Vitamin A, Vitamin byproducts of Vitamine A, and isomers thereof. One of the intermediates employed in the method of the application is isoprene chloroacetate (1-chloro-4-acetoxy-2-methyl-2-butene).

In addition to being useful in making Vitamin A and related products, the isoprene chloroacetate may also be a valuable intermediate in the synthesis of Vitamin E, in the synthesis of carotenoids and in the synthesis of many other terpenic and non-terpenic materials in which isoprene is a basic unit in the molecule. (See copending application Ser. No. 560,550, filed Mar. 20, 1975, by Ralph E. Close and William Oroshnik, on "Synthesis of Dehydrophytol and Vitamin E".)

The synthesis of isoprene-1,4-chloroacetate is known and is reported in the *Journal of the American Chemical Society*, Vol. 72, pages 4608–13, (1950) in an article by W. Oroshnik and R. A. Mallory. The synthesis involves the treatment of isoprene with tert-butyl hypochlorite in the presence of a large excess of acetic acid, and gives the desired 1,4-chloroacetate; namely the cis and trans forms of 1-chloro-4-acetoxy-2-methyl-2-butene (formula I above). Although not reported in the above article, this synthesis also gives a small amount of 4-chloro-1-acetoxy-2-methyl-2-butene (formula II) as follows:

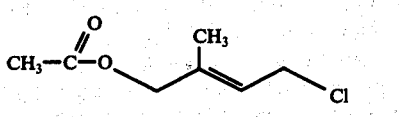

Unfortunately, the process also yields the 1,2 chloroacetate isomer, 1-chloro-2-acetoxy-2-methyl-3-butene (formula III), and a mixture of chloroethers, 1-chloro-4-tert-butoxy-2-methyl-2-butene (formula IV), and 4-chloro-1-tert-butoxy-2-methyl-2-butene (formula V).

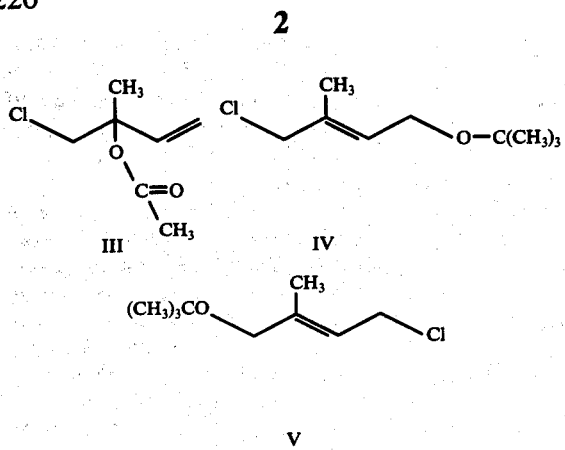

It was reported in the aforementioned article that the ratios of 1,4-chloroacetate (I) to 1,2-chloroacetate (III) to ethers (IV and V) was 32 : 20 : 5, with the ether (V) predominating over the ether (IV). The article further reported that the ethers could be converted using acetic anhydride and anhydrous $FeCl_3$, to the corresponding chloroacetates (I and II), respectively; and the 1,2 chloroacetate (III) could be converted to the 1,4-chloroacetate by treatment with glacial acetic acid containing sulfuric acid and copper sulfate ($CuSO_4 . H_2O$). If the catalyst was omitted, no reaction was observed.

A primary disadvantage with the Oroshnik and Mallory process resides in the additional process steps required to obtain a good yield of the desired 1,4-compounds; namely, at the very least, distillation of the crude product of the hypochlorite/isoprene reaction and work-up of 1,4-product, followed by sulfuric acid treatment of remaining 1,2-product and the chloroethers as described, redistillation, and a second work-up. Work-up itself is, of course, a process involving a series of process steps. Accordingly, the steps are numerous and the process is costly.

SUMMARY OF THE INVENTION

In accordance with the concepts of the present invention, the foregoing disadvantages of the Oroshnik and Mallory process can be overcome by subjecting a reaction mixture of isoprene, excess glacial acetic acid and tert-butyl hypochlorite, without any separation of reactants or products, to the addition of sulfuric acid ($H_2SO_4$) followed by stirring at about 50°. Surprisingly, this results in a high yield of 1,4-isoprene chloroacetate substantially free of the 1,2 isomer and the tert-butyl ethers. The desired 1-chloro-4-acetoxy-2-methyl-2-butene (Formula I) predominates in the product mixture over the 4-chloro-1-acetoxy-2-methyl-2-butene (Formula II) in the ratio of 96 : 4.

The invention is applicable to the preparation of haloallylic esters other than 1,4-isoprene chloroacetate, such as the 1,4-haloallylic esters of butadiene and pentadiene. In particular the present invention resides in its broadest aspect in the process of preparing a reaction mixture which consists essentially of a conjugated diene, a halogenating agent and a carboxylic acid, the improvement comprising treating said reaction mixture with a catalytic amount of a strong acid having a high dissocition constant and carrying out said treatment with the application of heat for a sufficient period of time to convert a substantial portion of 1,2-halo carboxylate and any haloethers in the reaction mixture to 1,4-halo carboxylate.

Particular dienes with which the present invention is applicable, in addition to isoprene, are butadiene, piperylene (1,3-pentadiene) and 1,3-octadiene, all capable of producing a mixed reaction product of 1,4-halo allylic ester and 1,2-halo allylic ester. By the present invention, the 1,4 -product predominates.

A preferred strong acid for the use in the process of the present invention is sulfuric acid. However, other suitable strong acids in addition to sulfuric acid, having a high dissociation constant, which are stable in the reaction medium ("stable" being defined as non-fugitive and non-reactive under the reaction conditions with the diene skeleton), are all mineral acids such as phosphoric acid, sulfurous acid, nitric acid, phosphorous acid, pyrophosphorous acid, iodic acid, periodic acid, and perchloric acid, and organic acids such as alkyl and aryl sulfonic acids; e.g., p-toluene sulfonic acid, dichloroacetic acid, trichloroacetic acid, oxalic acid, maleic acid, and picric acid. Also included are acid salts, such as sodium bisulfate and other sources of acid ions, e.g., bisulfate ion or similar ions, which act as strong proton donors, and ion exchange resins such as Amberlyst-15 (a sulfonic acid type ion exchange resin, trademark Rohm & Haas). The amount of strong acid is not particularly critical and it will be evident to those skilled in the art what is meant by a "catalytic amount". Normally, this will be about 0.02–0.5 mol strong acid, per mol of halogenating agent employed, preferably about 0.1 mol per mol of halogenating agent.

For purposes of the present application, the term "strong acid" has that meaning generally accepted in the art. Preferably, it means those acids having a dissociation constant above about $1 \times 10^{-3}$, preferably above about $1 \times 10^{-2}$.

Suitable carboxylic acids useful in preparation of the reaction mixture, in addition to acetic acid, include formic acid, propionic acid and other lower alkyl acids to eight carbon atoms, benzoic acid and other lower aralkyl acids. The halogenating agent can be any alkyl or aralkyl hypohalite, acyl hypohalite, halogens, mixed halogens and other sources of positive halogen ions.

Preferably, the carboxylic acid is employed in excess amount, for instance, in a mol ratio of 2–15 mols per mol of halogenating agent employed, a preferred ratio being about 6 : 1. Also the diene should be employed in excess amount over the halogenating agent, to suppress the formation tetrahalide, the tetrahlide, although the invention is applicable where the ratio varies from about 1 to 5. A preferred ratio is 1.25 mols diene per mol halogenating agent.

The temperature of the reaction mixture following addition of the strong acid can vary, for instance, from room temperature to about 100° C., the particular temperature selected depending upon the economies of the reaction. For instance, at low temperatures, the reaction may be too slow. At high temperatures some decomposition of product may occur. A preferred temperature is about 50° C.

The following example illustrates the present invention.

EXAMPLE 1

This example compares te chloroacetate reaction product obtained by conventional preparation of chloroacetate, according to the process reported in the Journal of the American Chemical Society (supra), with a reaction product obtained according to the concepts of the present invention. Two reaction mixtures were made up each employing 85 grams (1.25 mols) of isoprene dissolved in 360 grams (6.0 mols) of glacial acetic acid to which one mol of tert-butyl hypochlorite was added. One reaction mixture, according to the concepts of the present invention, prior to work-up, also had added to it 9.0 grams of concentrated sulfuric acid, and this reaction mixture was then stirred at 50° C. for 8 hours. The reaction products from both reaction mixtures were subjected to reflux stripping on a head column, under identical conditions, yielding the following products; Table 1 giving the products obtained by the conventional procedure of the Journal of the American Chemical Society, and Table 2 giving the products obtained by the concepts of the present invention.

TABLE 1

| Cut | Cut Wt. (grams) | 1,2-chloroacetate Wt. (grams) | % | chlorobutyl ether Wt. (grams) | % | 1,4-chloroacetate Wt. (grams) | % |
|---|---|---|---|---|---|---|---|
| 1 | 11 | 0.59 | 5.39 | — | — | 0.13 | 1.18 |
| 2 | 71 | 21.17 | 29.82 | 3.61 | 5.08 | 38.33 | 53.99 |
| 3 | 1 | 0.02 | 2.04 | — | — | — | — |
|   |   | 21.78 |   | 3.61 |   | 38.46 |   |

Total = 63.85 grams total

TABLE 2

| Cut | Wt. (grams) | 1,4-chloroacetate Wt. (grams) | % |
|---|---|---|---|
| 1 | 20 | 0 | 0 |
| 2 | 1 | .53 | 52.99 |
| 3 | 72 | 60.49 | 84.02 |
| 4 | 4 | 1.36 | 34.39 |

Total = 62.38 grams total

It is apparent from the above data that, whereas the overall total conversion yields of the two runs were essentially equivalent, the yield of 1,4-chloroacetate was substantially higher in the second run, in accordance with the concepts of the present invention. Specifically, the procedure in accordance with the present invention (Table 2) resulted in a yield of 62.38 grams of the 1,4-chloroacetate as compared with only 38.46 grams of the 1,4-chloroacetate (Table 1) following conventional synthesis procedures. As shown in Table 1, the conventional procedure also yielded 21.78 grams of the 1,2-chloroacetate and 3.61 grams of the chlorobutyl ether, an amount substantial enough to cause severe separation problems to obtain a relatively pure 1,4-chloroacetate product. In particular, it is necessary first to subject the crude product to the conventional steps of work-up, followed by distillation to obtain a 1,4-chloroacetate fraction and a fraction containing 1,2-product and the chloro ethers. Rigorous fractionation is required to obtain the desired 1,4-chloroacetate free of by-products. The 1,2- product fraction must then be treated, in accordance with the conventional procedure, with glacial acetic acid containing sulfuric acid and copper sulfate and worked-up followed by a second distillation. If conversion of the ethers to the corresponding acetates is desired, this may require a still further reaction step and additional work-up.

The concepts of the present invention may further be seen by analysis of samples of the reaction mixture taken at intervals after addition of $H_2SO_4$. Table 3 shows the relative proportions of the subject products prior to addition of $H_2SO_4$ and at intervals thereafter.

TABLE 3

|  | Prior to $H_2SO_4$ Add'n | Subsequent to $H_2SO_4$ Addition | | | | | |
| --- | --- | --- | --- | --- | --- | --- | --- |
|  |  | 2 hr. | 4 hr. | 5 hr. | 6 hr. | 7 hr. | 8 hr. |
| 1,2-chloroacetate | 34.0% | 13.9% | 6.9% | 5.1% | 3.5% | 1.1% | 0.9% |
| chloroethers | 5.5 | 1.9 | 1.9 | 1.6 | 1.7 | 0.8 | 1.6 |
| 1,4-chloroacetate | 60.4 | 84.2 | 91.2 | 93.3 | 94.7 | 98.1 | 97.5 |

I claim:

1. In a process for the synthesis of 1,4-haloallylic esters from $C_4$–$C_8$ conjugated alkadienes which comprises reacting the conjugated alkadiene, a halogenating agent and a carboxylic acid, said carboxylic acid being a compound selected from the group consisting of alkanoic acids having one to eight carbon atoms, and benzoic acid to form a reaction product mixture containing 1,4- and 1,2-halocarboxylates and 1,4-haloethers, the improvement comprising;
   a. adding to said reaction product mixture a catalytic amount of strong acid having a dissociation constant above about $1 \times 10^{-3}$; and
   b. stirring the mixture at room temperature to 100° C. for a sufficient period of time to convert a substantial portion of the 1,2-halocarboxylate product and haloethers in the reaction mixture to the 1,4-halocarboxylate product.

2. The process of claim 1 wherein said strong acid is sulfuric acid.

3. The process of claim 2 wherein the catalytic amount of strong acid is 0.02–0.5 mol acid per mol of halogenating agent, and the stirring is carried out at about 50° C.

4. The process of claim 3 wherein the reaction mixture comprises the following proportions:

| Halogenating agent | 1.0 mol |
| --- | --- |
| Diene | 1–5 mols |
| Carboxylic acid | 2–15 mols |
| Strong acid | 0.02–0.5 mol |

5. The process of claim 3 wherein the reaction mixture comprises the following approximate proportions:

| Halogenating agent | 1.0 mol |
| --- | --- |
| Diene | 1.25 mols |
| Carboxylic acid | 6.0 mols |
| Strong acid | 0.1 mol. |

6. The process of claim 1 wherein said alkadiene is isoprene.

7. In a process for the synthesis of 1-chloro-4-acetoxy-2-methyl-2-butene which comprises reacting isoprene with t-butyl hypochlorite in excess glacial acetic acid to form a reaction product mixture containing 1,4- and 1,2-chlorocarboxylates and 1,4-chloroethers; the improvement comprising
   a. adding a catalytic amount of product $H_2SO_4$ to said reaction mixture; and
   b. stirring the same at room temperature to 100° C for a reaction period sufficient to convert a substantial portion of 1,2-isoprene chloroacetate and chloroethers to 1-chloro-4-acetoxy-2-methyl-2-butene.

8. The process of claim 7 wherein the reaction components are employed in the following approximate proportions:

| Component | Mols |
| --- | --- |
| Isoprene | 1.25 |
| t-Butyl hypochlorite | 1.0 |
| Glacial acetic acid | 6.0 |
| Sulfuric acid | 0.1, | the stirring being carried out at about 50° C.

9. In the preparation of haloesters from $C_4$–$C_8$ conjugated alkadienes wherein said alkadienes are reacted with a chlorinating agent and a carboxylic acid selected from the group consisting of alkanoic acids having one to eight carbon atoms, and benzoic acid to form a reaction product mixture containing 1,4- and 1,2-chlorocarboxylates and 1,4-chloroethers, the improvement comprising the steps of adding to said reaction product mixture a catalytic amount of a strong acid having a high dissociation constant above about $1 \times 10^{-3}$, and stirring the mixture at room temperature to 100° C. for a sufficient period of time to convert a substantial proportion of the 1,2-chlorocarboxylate and 1,4-chloroethers to the 1,4-chlorocarboxylate.

* * * * *

UNITED STATES PATENT AND TRADEMARK OFFICE
CERTIFICATE OF CORRECTION

PATENT NO. : 4,048,220
DATED : September 13, 1977
INVENTOR(S) : Carlos G. Cardenas It is certified that error appears in the above-identified patent and that said Letters Patent are hereby corrected as shown below:

Col. 1, line 30, change "Vitamin", second occurrence, to --carotenoid--; line 31, change "Vitamine" to --Vitamin--. Col. 2, line 64, change "dissocition" to --dissociation--. Col. 3, line 59, delete "the tetrahlide,". Col. 4, line 7, change "te" to --the--. Col. 6, line 22, delete "product"; line 23, after "reaction" insert --product--; line 49, in claim 9, delete "high". Col. 3, line 59, after "formation" insert -- of the --.

Signed and Sealed this

*Twenty-seventh* Day of *December 1977*

[SEAL]

Attest:

RUTH C. MASON
*Attesting Officer*

LUTRELLE F. PARKER
*Acting Commissioner of Patents and Trademarks*